United States Patent [19]

Aichaioui et al.

[11] Patent Number: 5,147,883

[45] Date of Patent: Sep. 15, 1992

[54] ACYLBENZOXAZOLINONES COMPOUNDS

[75] Inventors: Hocine Aichaioui, Lille; Daniel Lesieur, Gondecourt; Charles Lespagnol, Lambersart; Michelle Devissaguet; Beatrice Guardiola, both of Neuilly Sur Seine, all of France

[73] Assignee: Adir et Compagnie, Courbevoie, France

[21] Appl. No.: 708,515

[22] Filed: May 31, 1991

[30] Foreign Application Priority Data

Jun. 22, 1990 [FR] France .................. 90 07812

[51] Int. Cl.$^5$ ............ A61K 31/42; C07D 263/58
[52] U.S. Cl. ................... 514/338; 514/307; 514/314; 514/375; 546/146; 546/168; 546/270; 548/221
[58] Field of Search .......... 546/146, 168, 270; 548/221; 514/307, 314, 338, 375

[56] References Cited

U.S. PATENT DOCUMENTS 4,558,020 12/1985 Caignard et al. .................. 548/221

OTHER PUBLICATIONS

Bonte, et al., (I) "Chemical Abstracts", vol. 82, 1975, col. 111989s.
Bonte, et al., (II), "Chemical Abstracts", vol. 82, 1975, col. 111990k.
Lespagnol, et al., (I), "Chemical Abstracts", vol. 82, 1975, col. 139692p.
Lespagnol, et al. (II), "Chemical Abstracts", vol. 82, 1975, col. 170878c.
Trottier, et al., "Chemical Abstracts", vol. 102, 1984, col. 102:12280d.

*Primary Examiner*—C. Warren Ivy
*Assistant Examiner*—James H. Turnipseed
*Attorney, Agent, or Firm*—Gordon W. Hueschen

[57] ABSTRACT

Compounds of general formula (I):

in which:

$R_1$ represents a hydrogen atom or a lower alkyl group,

A represents a hydrogen atom, and in this case B represents a group CO-G, G being:
  either a heteroaryl group selected from furan, indole, pyrrole, pyridine, quinoline, isoquinoline and benzofuran, optionally substituted with one or more lower alkyl or lower alkoxy groups or a halogen atoms,
  or a linear or branched lower alkyl group substituted with a carboxyl group,
  or a linear or branched lower alkenyl group substituted with a carboxyl group,
  or a phenyl or naphthyl group substituted with a carboxyl group,
  or alternatively A forms with B a group $CO(CH_2)_nCH(CH_3)$ with n being a integer equal to 1, 2, 3 or 4, the CO group being attached to the aromatic ring of the benzoxazolinone at the 5- or 6-position, as well as, where appropriate, their isomers and, when the compound of formula (I) possesses a carboxylic acid group, their addition salts with a pharmaceutically acceptable base, and, when the compound of formula (I) contains a basic group, their addition salts with a pharmaceutically acceptable acid, it being understood that lower alkyl and lower alkenyl mean linear or branched groups comprising from 1 to 6 carbon atoms.

Medicinal products.

9 Claims, No Drawings

ACYLBENZOXAZOLINONES COMPOUNDS

The present invention relates to new acylbenzoxazolinones, to a process for preparing them and to pharmaceutical compositions containing them.

Many benzoxazolinone compounds have been described in therapy.

More especially, Patents FR 73-23281 and FR 73-23280 as well as the publications Eur. J. Med. Chem. 1974, 9, (5), 491-496 and ibid. 497-500 describe analgesic and anti-inflammatory 6-acylbenzoxazolinones.

The Applicant has now discovered acylbenzoxazolinones endowed with advantageous antithromboxane properties which differ these compounds from the prior art.

More specifically, the invention relates to compounds of general formula (I):

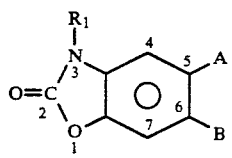

in which:
R₁ represents a hydrogen atom or a lower alkyl group, A represents a hydrogen atom, and in this case B represents a group CO—G, G being:
either a heteroaryl group selected from furan, indole, pyrrole, pyridine, quinoline, isoquinoline and benzofuran, optionally substituted with one or more lower alkyl or lower alkoxy groups or a halogen atoms,
or a linear or branched lower alkyl group substituted with a carboxyl group,
or a linear or branched lower alkenyl group substituted with a carboxyl group,
or a phenyl or naphthyl group substituted with a carboxyl group,
or alternatively A forms with B a group CO(CH₂)$_n$CH(CH₃) with n being an integer equal to 1, 2, 3 or 4, the CO group being attached to the aromatic ring of the benzoxazolinone at the 5- or 6-position,
as well as, where appropriate, their isomers and, when the compound of formula (I) possesses a carboxylic acid group, their addition salts with a pharmaceutically acceptable base, and, when the compound of formula (I) contains a basic group, their addition salts with a pharmaceutically acceptable acid, it being understood that lower alkyl, lower alkoxy and lower alkenyl mean linear or branched groups comprising from 1 to 6 carbon atoms.

Among pharmaceutically acceptable acids which can, where appropriate, be added to the compounds of formula (I) containing a basic group to obtain a salt, hydrochloric, sulfuric, tartaric, maleic, fumaric, oxalic, methanesulfonic and camphoric acids, and the like, may be mentioned without implied limitation.

Among pharmaceutically acceptable bases which can, where appropriate, be added to the compounds of formula (I) containing a carboxylic acid group to obtain a salt, sodium, potassium, calcium or aluminum hydroxides, alkali metal or alkaline earth metal carbonates or organic bases such as triethylamine, benzylamine, diethanolamine, tert-butylamine, dicyclohexylamine, arginine, and the like, may be mentioned without implied limitation.

The subject of the present invention is also the process for preparing the compounds of formula (I), wherein a compound of formula (II):

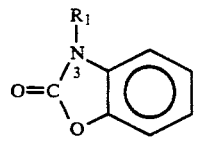

in which R₁ has the same definition as in the formula (I), is used as the starting material, which compound is treated in the presence of dimethylformamide and aluminum chloride:

a) either:
with an acid chloride of formula (III):

 ClCOG (III)

in which:
G has the same definition as in the formula (I), with the exception of the case where G represents a lower alkenyl group substituted with a carboxyl,
or with an acid anhydride of formula (IV):

 O(OCG)₂ (IV)

in which G has the same definition as in the formula (I),
to obtain a compound of formula (I/a):

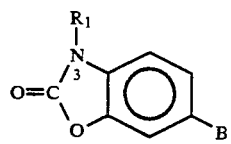

a special case of the compounds of formula (I) in which A represents a hydrogen atom and B has the same meaning as in the formula (I) when A represents a hydrogen atom, which compound of formula (I/a) is purified, if necessary, by a conventional technique selected from crystallization and chromatography, the isomers of which compounds are separated, where appropriate, and which compound is salified, if so desired, with a pharmaceutically acceptable base when B contains a carboxylic acid group, and with a pharmaceutically acceptable acid when B contains a basic group, b) or with an acid chloride of formula (V):

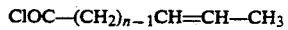 ClOC—(CH₂)$_{n-1}$CH=CH—CH₃ (V)

in which n has the same definition as in the formula (I),
or with a compound of formula:

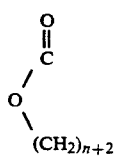

in which n has a same definition as in the formula (I), to obtain a mixture of compounds of formula (I/b):

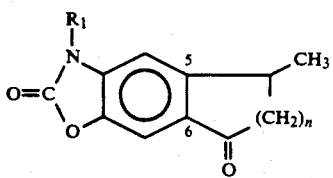

(I/b)

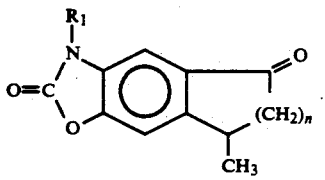

in which $R_1$ and n have the same definition as in the formula (I), a special case of compounds of formula (I) in which A forms with B a group $CO(CH_2)_nCHCH_3$, in which n has the same definition as in the formula (I), the CO group being attached either at the 5-position or at the 6-position of the benzoxazolinone, which compounds of formula (I/b) are separated and purified by one or more techniques selected from crystallization and chromatography.

A special case of the compound of the present invention relates to the compounds of formula (I/c):

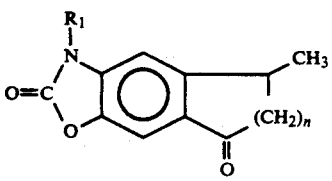

(I/c)

in which $R_1$ and n have the same definition as in the formula (I), which may be obtained by the action of aluminum chloride in the presence of dimethylformamide on a compound of formula (IV):

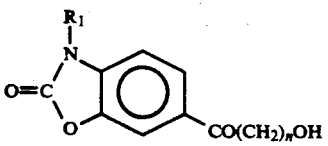

(IV)

in which $R_1$ and n have the same definition as in the formula (I), to obtain a compound of formula (I/c) which is purified, if so desired, by one or more techniques selected from crystallization and/or chromatography.

The compounds of formula (I) possess advantageous pharmacological properties.

A pharmacological study of the compounds of the invention showed, in effect, that they were of low toxicity and were endowed with antithromboxane activity.

This spectrum of activity hence renders the compounds of the present invention advantageous in a number of indications such as the treatment and the prevention of acute peripheral arterial ischemic attacks and stroke.

The subject of the present invention is also pharmaceutical compositions containing the products of the formula (I), alone or in combination with one or more pharmaceutically acceptable, non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like.

The appropriate dosage varies according to the patient's age and weight, the administration route and the nature of the therapeutic indication or of any associated treatments, and ranges between 0.5 centrigram and 4 grams per 24 hours.

The examples which follow illustrate the invention and in no way limit it.

The infrared spectra are carried out in a potassium bromide disk.

EXAMPLE 1

3-Methyl-6-nicotinoylbenzoxazolinone 9.9 ml (0.13 mol) of dimethylformamide are introduced dropwise and with stirring into a 250-ml flask containing 61.3 g (0.46 mol) of aluminum chloride.

The flask is equipped with a reflux condenser and taken to an oil bath at a temperature in the region of 45° C. 6 g (0.04 mol) of 3-methylbenzoxazolinone and 10.6 g (0.06 mol) of nicotinoyl chloride hydrochloride are introduced.

The mixture is heated to the temperature t 100°-110° C.) for a time θ (80 hours). The reaction mixture is poured into a sufficient quantity of ice, the resulting mixture is stirred for one hour and the precipitate formed is drained, washed with water and dried. It is recrystallized in ethanol.

Yield: 68%
Melting point: 163°-164° C.
Elemental analysis:
Calculated C: 66.13; H: 3.96; N: 11.02;
Found: C: 66.24; H: 3.96; N: 10.87.
Spectral characteristics:
Infrared:
1770 cm$^{-1}$: ν C═O (OCON);
1635 cm$^{-1}$: ν C═O (ketonic);
1600-1580 cm$^{-1}$: νC═C (aromatic),
Nuclear magnetic resonance (Solvent DMSO-d$_6$)
δ: 3.08 ppm, singlet 3H N—CH$_3$

EXAMPLE 2

6-Nicotinoylbenzoxazolinone (Hydrochloride)

The procedure described in Example 1 is used, replacing 3-methylbenzoxazolinone by benzoxazolinone.
θ: 30 hours
Yield: 60%
Melting point: 259°-260° C.
Elemental analysis:
Calculated C: 56.43; H: 3.28; N: 10.12;
Found C: 56.30; H: 3.35; N: 10.00.
Spectral characteristics:
Infrared:
1775 cm$^{-1}$: ν CO (OCON);
1645 cm$^{-1}$: ν CO (ketonic),
1610-1580 cm$^{-1}$: ν C═C (aromatic)
Nuclear magnetic resonance (Solvent DMSO d$_6$)
δ: 7.26 ppm, doublet (1H), H$_4$, J═8.8Hz;
δ: 6.68 ppm, doublet (1H), H$_7$, J═2.2Hz;

δ: 6.70 ppm, doublet of doublet (1H), H$_5$, J=8.8Hz; J=2.2Hz.

EXAMPLE 3

6-Furoyl-3-Methylbenzoxazolinone

Using the procedure described in Example 1, but replacing nicotinoyl chloride hydrochloride by 2-furoylchloride, the product of the title is obtained.
t: 95°-100° C.
θ: 4H30 min
Yield: 72%
Melting point: 140°-141° C.
Elemental analysis:
Calculated C: 64.19; H: 3.67; N: 5.67;
Found C: 64.26; H: 3.63; N: 5.86.
Spectral characteristics:
Infrared:
1760 cm$^{-1}$: ν CO (OCON);
1625 cm$^{-1}$: ν CO (ketonic);
1600 cm$^{-1}$: ν C=C (aromatic);
Nuclear magnetic resonance (Solvent DMSO d$_6$)
δ: 3.41 ppm, singlet 3H, N—CH$_3$;
δ: 7.40 ppm, doublet, 1H, (H$_4$), J=7.7Hz;
δ: 7.84 ppm, singlet, 1H, (H$_7$);
δ: 7.94 ppm, doublet of doublet, 1H, (H$_5$), J=7.7Hz; J=1.6Hz.

EXAMPLE 4

6-Furoylbenzoxazolinone

Using the procedure described in Example 2, but replacing nicotinoyl chloride hydrochloride by 2-furoyl chloride, the product of the title is obtained.
t: 95°-100° C.
θ: 5H
Yield: 68%
Melting point: 233°-234° C.
Elemental Analysis:
Calculated C: 62.88; H: 3.08; N: 6.11;
Found C: 62.55; H: 3.11; N: 5.97.
Spectral characteristics:
Infrared:
3100 cm$^{-1}$: μ NH;
1775 cm$^{-1}$: ν CO (OCON);
1620 cm$^{-1}$: ν CO (ketonic);
1583 cm$^{-1}$: ν C=C (aromatic).
$^1$H Nuclear aromatic resonance (Solvent DMSO d$_6$)
δ: 7.24 ppm, doublet, 1H, (H$_4$), J=7.6Hz,
δ: 7.80 ppm, singlet, 1H, H$_7$;
δ: 7.85 ppm, doublet of doublet, 1H, H$_5$, J=7.6Hz.

EXAMPLE 5

4-Oxo-4-(3-methylbenzoxazolinon-6-yl)butyric acid 8.6 ml (0.115 mol) of dimethylformamide are introduced dropwise and with stirring into a 250-ml flask containing 53.3 g (0.4 mol) of aluminum chloride. The flask is equipped with a reflux condenser and taken to an oil bath at a temperature in the region of 45° C.

6 g (0.04 mol) of 3-methylbenzoxazolinone and 6 g of succinic anhydride (0.06 mol) are introduced. The mixture is heated to 90°-95° C. (temperature t) for a time θ (5H30 minutes).

The reaction mixture is poured into a sufficient quantity of ice, the resulting mixture is stirred for one hour and the precipitate formed is drained. The product obtained is taken up with 10% aqueous sodium bicarbonate solution. The alkaline solution is extracted several times with ether and the aqueous phase is then acidified with dilute hydrochloride acid. The precipitate obtained is drained, washed with water, dried and recrystallized in ethanol.
Yield: 62%
Melting point: 179°-180° C.
Elemental analysis:
Calculated C: 57.83; H: 4.44; N: 5.62;
Found C: 57.62; H: 4.53; N: 5.83.
Spectral characteristics:
Infrared:
3300 cm$^{-1}$: ν OH (acid);
1750 cm$^{-1}$: ν (N—CO—O);
1730 cm$^{-1}$: ν CO (acid);
1660 cm$^{-1}$: ν CO (ketonic);
1600 cm$^{-1}$: ν C=C (aromatic).
Nuclear magnetic resonance (Solvent: acetone-d$_6$)
δ: 3.36 ppm, triplet, 2H, CO—CH$_2$
δ: 3.50 ppm, singlet, 3H, N—CH$_3$

EXAMPLE 6

4-Oxo-4-(benzoxazolinon-6-yl)butyric acid

Using the procedure described in Example 5, but replacing 3-methylbenzoxazolinone by benzoxazolinone, the product of the title is obtained.
t: 90°-95° C.
θ: 5H30 min
Recrystallization solvent: Ethanol/water (1:4)
Yield: 54%
Melting point: 218°-219° C.
Spectral characteristics:
Infrared:
3290 cm$^{-1}$: ν OH (acid:
3060 cm$^{-1}$: ν NH;
1740 cm$^{-1}$: ν CO (OCON);
1670 cm$^{-1}$: ν CO (ketonic);
1705 cm$^{-1}$: ν CO (acid).
Nuclear magnetic resonance (Solvent: acetone-d$_6$)
δ: 2.74 ppm, triplet, 2H, CH$_2$—COOH;
δ: 3.33 ppm, triplet, 2H, CO—CH$_2$.

EXAMPLE 7

2-Methyl-4-oxo-4-(3-methylbenzoxazolinon-6-yl)butyric acid

Using the procedure described in Example 5, but replacing succinic anhydride by methylsuccinic anhydride, the product of the title is obtained.
Temperature t: 80°-85° C.
θ: 4H30 min
Recrystallization solvent: water/ethanol (4:2)
Yield: 43%
Melting point: 186°-187° C.
Elemental Analysis:
Calculated C: 59.31; H: 4.98; N: 5.32;
Found C: 59.17; H: 4.90; N: 5.39.
Spectral characteristics:
Infrared:
3060-2880 cm$^{-1}$: μ OH (acid);
1770 cm$^{-1}$: ν CO (OCON);
1700 cm$^{-1}$: ν CO (acid);
1670 cm$^{-1}$: ν (ketonic).
Nuclear aromatic resonance (Solvent: DMSO d$_6$)
δ: 1.18 ppm, doublet, 3H, CH$_3$CH—COOH
δ: 2.90 to 3.64 ppm, unresolved complex, 6H, N—CH$_3$ and CH$_2$—CH—COOH

EXAMPLE 8

2-Methyl-4-oxo-4-(benzoxazolinon-6-yl)butyric acid

Using the procedure described in Example 7, but replacing 3-methylbenzoxazolinone by benzoxazolinone, the product of the title is obtained.

Temperature t: 80°-85° C.
θ: 4H30 min
Recrystallization solvent: water/ethanol (5:0.5)
Yield: 32%
Melting point: 206°-208° C.
Elemental Analysis:
Calculated C: 57.83; H: 4.45; N: 5.62;
Found C: 57.61; H: 4.35; N: 5.52.
Spectral characteristics:
Infrared:
3210-2900 cm$^{-1}$: μ NH and OH (acid);
1760 cm$^{-1}$: ν CO (OCON);
1690 cm$^{-1}$: ν CO (acid);
1675 cm$^{-1}$: ν CO (ketonic).
Nuclear aromatic resonance (Solvent: DMSO d$_6$)
δ: 1.19 ppm, doublet, 3H, CH$_3$CH—COOH;
δ: 2.73 to 3.62 ppm, unresolved complex, 3H, CH$_2$—CH—COOH

EXAMPLE 9

4-Oxo-4-(3-methybenzoxazolinon-6-yl)-2-butenoic acid

Using the procedure described in Example 5, but replacing succinic anhydride by maleic anhydride, the product of the title is obtained.

Temperature t: 80° C.
θ: 4H30 min
Recrystallization solvent: EtOH
Yield: 58%
Melting point: 220°-221° C.
Elemental Analysis:
Calculated C: 58.30; H: 3.67; N: 5.67;
Found C: 58.06; H: 3.88; N: 5.65.
Spectral characteristics:
Infrared:
3280 cm$^{-1}$: μ OH (acid);
1760 cm$^{-1}$: ν CO (NCOO);
1720 cm$^{-1}$: ν CO (acid);
1655 cm$^{-1}$: ν CO (ketonic).
Nuclear aromatic resonance (Solvent: DMSO d$_6$)
δ: 3.41 ppm, doublet, 3H, N—CH$_3$

EXAMPLE 10

4-Oxo-4-(benzoxazolinon-6-yl)-2-butenoic acid

Using the procedure described in Example 9, but replacing 3-methylbenzoxazolinone by benzoxazolinone, the product of the title is obtained.

Temperature t: 80° C.
θ: 4H30 min
Recrystallization solvent: water
Yield: 49%
Melting point: 235°-236° C.
Elemental Analysis:
Calculated C: 56.65; H: 3.03; N: 6.00;
Found C: 56.69; H: 3.25; N: 6.03.
Spectral characteristics:
Infrared:
3220 cm$^{-1}$: μ OH (acid);
3000 cm$^{-1}$: ν NH;
1755 cm$^{-1}$: ν CO (OCON);
1700 cm$^{-1}$: ν CO (acid);
1650 cm$^{-1}$: ν CO (ketonic);
Nuclear magnetic resonance (Solvent: DMSO d$_6$)
δ: 7.80 ppm, doublet, 1H, H$_4$, J$_{4-5}$=7.5 Hz;
δ: 7.85 ppm, singlet, 1H, H$_7$;
δ: 7.90 ppm, doublet, 1H, H$_5$, J$_{5-4}$=7.5Hz.

EXAMPLE 11

2-Methylene-4-oxo-4-(3-methylbenzoxazolinon-6-yl)butyric acid

Using the procedure described in Example 5, but replacing succinic anhydride by itaconic anhydride, the product of the title is obtained.

Temperature t: 75°-80° C.
θ: 4H30 min
Yield: 46%
Recrystallization solvent: ethanol
Melting point: 180° C.
Elemental analysis:
Calculated C: 59.77; H: 4.24; N: 5.36;
Found C: 59.96; H: 4.19; N: 5.84.
Spectral characteristics:
Infrared:
3100 to 2800 cm$^{-1}$: ν OH (acid)
1745 cm$^{-1}$: ν NH
1710 cm$^{-1}$: ν CO (acid)
1670 cm$^{-1}$: ν CO (ketonic
Nuclear magnetic resonance (Solvent: DMSO-d$_6$)
δ: 3.34 ppm, singlet, 3H, N—CH$_3$;
δ: 4.02 ppm, singlet, 2H, CO—CH$_2$;
δ: 7.90 ppm, doublet, 1H, H$_5$, J$_{5-4}$=7.5Hz

EXAMPLE 12

2-Methylene-4-oxo-4-(benzoxazolinon-6-yl)butyric acid

Using the procedure described in Example 11, but replacing 3-methylbenzoxazolinone by benzoxazolinone, the product of the title is obtained.

Temperature t: 75°-80° C.
θ: 5H
Recrystallization solvent: water/ethanol (1:1)
Yield: 34%
Melting point: 222°-223° C.
Elemental analysis:
Calculated C: 58.30; H: 3.67; N: 5.67;
Found C: 58.79; H: 3.38; N: 5.20.
Spectral characteristics:
Infrared:
3300 cm$^{-1}$: λ OH (acid)
3080 cm$^{-1}$: λ NH
1745 cm$^{-1}$: λ CO (OCON)
1695 cm$^{-1}$: λ CO (acid)
1615 cm$^{-1}$: λ CO (ketonic
1605 cm$^{-1}$: λ C=C (aromatic)
Nuclear magnetic resonance (Solvent: DMSO-d$_6$)
δ: 7.18 ppm, doublet, 1H, H$_4$, J$_{4-5}$=8.4Hz;
δ: 7.81 ppm, singlet, 1H, H$_7$;
δ: 7.87 ppm, doublet, 1H, H$_5$, J$_{5-4}$=8.4Hz.

EXAMPLE 13

2-[(3-Methylbenzoxazolinon-6-yl)carbonyl]benzoic acid

Using the procedure described in Example 5, but replacing succinic anhydride by phthalic anhydride, the product of the title is obtained.

Temperature t: 95°-100° C.
θ: 8H
Recrystallization solvent: ethanol

Yield: 58%
Melting point: 210°–211° C.
Elemental analysis:
Calculated C: 64.63; H:3.73; N: 4.71;
Found C: 64.14; H: 3.92; N: 4.74.
Spectral characteristics:
Infrared:
3460 cm$^{-1}$: λ OH;
1775 cm$^{-1}$: λ CO (OCON);
1680 cm$^{-1}$: λ CO (acid);
1640 cm$^{-1}$: λ CO (ketonic).
Nuclear magnetic resonance (Solvent: DMSO-d$_6$)
δ: 3.36 ppm, 3H, N—CH$_3$
δ: 7.26 ppm, doublet, 1H, (H$_4$), J$_{4-5}$=8.7Hz
δ: 7.68 ppm, doublet of doublet, 1H, (H$_5$) J$_{5-4}$=8.7Hz

EXAMPLE 14

2-[(Benzoxazolinon-6-yl)carbonyl]benzoic acid

Using the procedure described in Example 13, but replacing 3-methylbenzoxazolinone by benzoxazolinone, the product of the title is obtained.
Temperature t: 95°–100° C.
θ: 8H
Recrystallization solvent: water/ethanol (3:1)
Yield: 52%
Melting point: 243°–244° C.
Elemental analysis:
Calculated C: 63.60; H: 3.20; N: 4.94;
Found C: 63.29; H: 3.18; N: 4.92.
Spectral characteristics:
Infrared:
3470 cm$^{-1}$: λ OH (acid);
3360 cm$^{-1}$: λ NH;
1770 cm$^{-1}$: λ CO (OCON);
1690 cm$^{-1}$: λ CO (acid);
1650 cm$^{-1}$: λ CO (ketonic).
Nuclear magnetic resonance (Solvent: DMSO-d$_6$)
δ: 7.15 ppm, doublet, 1H (H$_4$), J$_{4-5}$=8.5Hz;
δ: 7.70 ppm, doublet of doublet, 1H, (H$_5$), J$_{5-4}$=8.5Hz.

EXAMPLE 15

2,3-dihydro-2,5-dioxo-3,7-dimethylcyclopenta[f]benzoxazole

Using the procedure described in Example 5, but replacing succinic anhydride by crotonyl chloride or alternatively γ-butyrolactone, the product of the title is obtained.
It is purified by chromatography on a column of silica gel with a 1:5 cyclohexane/ethyl acetate mixture.
Temperature t: 80°–85° C.
θ: 2H30 min to 3H
Recrystallization solvent: ethanol
Yield: 52%
Melting point: 166°–167° C.
Elemental analysis:
Calculated C: 66.35; H: 5.10; N: 6.45;
Found C: 66.18; H: 5.17; N: 6.39.
Spectral characteristics:
Infrared:
1770 cm$^{-1}$: λ CO (OCON);
1680 cm$^{-1}$: λ CO (ketonic).
Nuclear magnetic resonance (Solvent: DMSO-d$_6$)
δ: 1.34 ppm, doublet, 3H HC—CH$_3$, J=6.6Hz;
δ: 3.36 ppm, singlet, 3H, N—CH$_3$

EXAMPLE 16

2,3-Dihydro-2,7-dioxo-3,5-dimethylcyclopenta[f]benzoxazole 8.6 ml (0.115 mol) of dimethylformamide are introduced dropwise and with stirring into a 250-ml flask containing 53.3 g (0.4 mol) of aluminum chloride. The flask is equipped with a reflux condenser and taken to an oil bath at a temperature in the region of 45° C. 6 g (0.04 mol) of 6-(4-hydroxybutyryl)-3-methylbenzoxazolinone are introduced and the mixture is heated to 90° C. for 2 hours.

The reaction medium is hydrolyzed and the procedure is then as described in Example 5.
Yield: 52%
Melting point: 189° C.
Recrystallization solvent: ethanol
Elemental analysis:
Calculated C: 66.35; H: 5.10; N: 6.45;
Found C: 66.19; H: 5.21; N: 6.43.
Spectral characteristics:
Infrared:
1770 cm$^{-1}$: λ CO (OCON);
1695 cm$^{-1}$: λ CO (ketonic).
Nuclear magnetic resonance (Solvent: DMSO-d$_6$)
δ: 1.38 ppm, doublet, 3H, CH—CH$_3$), J=7Hz;
δ: 3.39 ppm, singlet, 3H, N—CH$_3$ N.B. This compound may be obtained using the same procedure as that described in Example 15. The two compounds are separated by chromatography, Example 16 being eluted second.

EXAMPLE 17

2,3-Dihydro-2,5-dioxo-7-methylcyclopenta[f]benzoxazole

Using the procedure described in Example 15, but replacing 3-methylbenzoxazolinone by benzoxazolinone, the product of the title is obtained.
Recrystallization solvent: EtOH/water (2:4)
Melting point: 252°–253° C.
Elemental analysis:
Calculated C: 65.02; H: 4.47; N: 6.89;
Found C: 64.77; H: 4.37; N: 6.84.
Spectral characteristics:
Infrared:
1770 cm$^{-1}$: λ CO (O—CO—N);
1680 cm$^{-1}$: λ CO (ketonic).
Nuclear magnetic resonance (Solvent: DMSO-d$_6$)
δ: 1.36 ppm, doublet, 3H, CH—CH$_3$

EXAMPLE 18

2,3-Dihydro-2,7-dioxo-5-methylcyclopenta[f]benzoxazole

Using the procedure described in Example 16, and replacing 6-(4-hydroxbutyryl)-3-methylbenzoxazolinone by 6-(4-hydroxybutyryl)benzoxazolinone, the product of the title is obtained.
Melting point: 213°–214° C.
Recrystallization solvent: ethanol/water 1/2 (v/v) (2:4)
Elemental analysis:
Calculated C: 65.02; H: 4.47; N: 6.89;
Found C: 64.72; H: 4.70; N: 6.98.
Spectral characteristics:
Infrared:
1780 cm$^{-1}$: λ CO (OCON);
1775 cm$^{-1}$: λ CO (ketonic).
Nuclear magnetic resonance (Solvent: DMSO-d$_6$)

δ: 1.32 ppm, doublet, 3H, C—CH₃, J=6.6Hz
N.B. This compound may be obtained using the same procedure as that described for Example 17. The two compounds are separated by chromatography. Example 18 is eluted second.

EXAMPLE 19

2,3-Dihydro-8-methyl-2,5-dioxocyclohexa[f]benzoxazole

Using the procedure described in Example 17, but replacing crotonyl chloride or γ-butyrolactone by δ-valerolactone, the product of the title is obtained.

It is purified by chromatography on a column of silica gel with a cyclohexane/ethyl acetate (1:5) mixture.
Temperature t: 90°–95° C.
Heating time: 4H–4H30 min
Melting point: 244°–245° C.
Yield: 80%
Recrystallization solvent: (ethanol)
Elemental analysis:
Calculated C: 66.35; H: 5.10; N: 6.44;
Found C: 66.13; H: 4.92; N: 6.86.
Spectral characteristics:
Infrared:
3300 cm⁻¹: λ NH;
1775 cm⁻¹: λ CO (OCON);
1660 cm⁻¹: λ CO (ketonic).
Nuclear magnetic resonance (Solvent: DMSO-d₆)
δ: 1.35 ppm, doublet, 3H, C—CH₃, J=6.5Hz

EXAMPLE 20

2,3-Dihydro-5-methyl-2,8-dioxocyclohexa[f]benzoxazole

Using the procedure described in Example 19, the product of the title is obtained during the purification by chromatography.
Melting point: 247°–248° C.
Yield: 20%
Elemental analysis:
Calculated C: 66.35; H: 5.10; N: 6.44;
Found C: 66.57; H: 5.54; N: 6.09.
Spectral characteristics:
Infrared:
3300 cm⁻¹: λ NH;
1780 cm⁻¹: λ CO (OCON);
1650 cm⁻¹: λ CO (ketonic).
Nuclear magnetic resonance (Solvent: DMSO-d₆)
δ: 1.36 ppm, doublet, 3H, C—CH₃, J=6.7Hz

EXAMPLE 21

2,3-Dihydro-3,8-dimethyl-2,5-dioxocyclohexa[f]benzoxazole

The procedure described in Example 19 is used, replacing benzoxazolinone by 3-methylbenzoxazolinone.
Recrystallization solvent: cyclohexane
Yield: 80%
Melting point: 114°–115° C.
Elemental analysis:
Calculated C: 67.52; H: 5.66; H: 6.06;
Found C: 67.63; H: 5.51; H: 5.99.
Spectral characteristics:
Infrared:
1770 cm⁻¹: λ CO (OCON);
1660 cm⁻¹: λ CO (ketonic).
Nuclear magnetic resonance (Solvent: DMSO-d₆)
δ: 1.39 ppm, doublet, 3H, C—CH₃, J=6.5Hz
δ: 3.35 ppm, singlet, 3H, N—CH₃

EXAMPLE 22

3-Methyl-6-isonicotinoylbenzoxazolinone(hydrochloride)

Using the procedure described in Example 1, but replacing nicotinoyl chloride hydrochloride by isonicotinoyl chloride hydrochloride, the product of the title is obtained.

EXAMPLE 23

3-Methyl-6-(2-quinolycarbonyl)benzoxazolinone

Using the procedure described in Example 1, but replacing nicotinoyl chloride hydrochloride by 2-quionolinecarbonyl chloride hydrochloride, the product of the title is obtained.

EXAMPLE 24

6-(3-Quinolycarbonyl)benzoxazolinone

Using the procedure described in Example 2, but replacing nicotinoyl chloride hydrochloride by 3-quionolinecarbonyl chloride hydrochloride, the product of the title is obtained.

EXAMPLE 25

3-Methyl-6-(3-indolylcarbonyl)benzoxazolinone

Using the procedure described in Example 1, but replacing nicotinoyl chloride hydrochloride by 3-indolecarbonyl chloride (prepared as in Belgian Patent Application BE 900425), the product of the title is obtained.

EXAMPLE 26

3-Methyl-6-(2-Pyrrolylcarbonyl)benzoxazolinone

Using the procedure described in Example 1, but replacing nicotinoyl chloride hydrochloride by 2-pyrrolecarbonyl chloride, the product of the title is obtained.

EXAMPLE 27

6-(1-Isoquinolylcarbonyl)benzoxazolinone

Using the procedure described in Example 2, but replacing nicotinoyl chloride hydrochloride by 1-isoquinoinecarbonyl chloride hydrochloride, the product of the title is obtained.

EXAMPLE 28

6-[(1-Methyl-2-pyrrolyl)carbonyl]benzoxazolinone

Using the procedure described in Example 2, but replacing nicotinoyl chloride hydrochloride by 1-methyl-2-pyrrolecarbonyl chloride hydrochloride, the product of the title is obtained.

EXAMPLE 29

6-[(1-Methyl-2-Indolyl)carbonyl]benzoxazolinone

Using the procedure described in Example 2, but replacing nicotinoyl chloride hydrochloride by 1-methyl-2-indolecarbonyl chloride, the product of the title is obtained.

EXAMPLE 30

3-Methyl-6-[(5-methoxy-2-indolylcarbonyl]benzoxazolinone

Using the procedure described in Example 1, but replacing nicotinoyl chloride hydrochloride by 5- methoxy-2-indolecarbonyl chloride, the product of the title is obtained.

EXAMPLE 31

3-Methyl-6-[(5-chloro-2-indolyl)carbonyl]benzoxazolinone

Using the procedure described in Example 1, but replacing nicotinoyl chloride hydrochloride by 5-chloro-2-indolecarbonyl chloride, the product of the title is obtained.

PHARMACOLOGICAL STUDY OF THE COMPOUNDS OF THE INVENTION

EXAMPLE 32

Study of the Acute Toxicity

The acute toxicity was assessed after the oral administration of a dose of 650 mg.kg$^{-1}$ to batches of 8 mice (26±2 grams). The animals were observed at regular intervals during the first day, and daily during the 2 weeks following the treatment.

It is apparent that the compounds of the invention are completely non-toxic. No deaths are observed after administration of a dose of 650 mg.kg$^{-1}$. No disorders are noted after administration of this dose.

EXAMPLE 33

Study of the Platelet Aggregation-Inhibitory Activity

A platelet-rich plasma is prepared from citrated human blood obtained from donors who have taken no medication during the ten days preceding the drawing of the samples.

Platelet aggregation in this plasma medium is studied by turbidimetry employing arachidonic acid. The products of the invention are added to the plasma three minutes before the agonist. The products manifest significant platelet aggregation-antagonist activity.

EXAMPLE 34

Pharmaceutical Composition: Tablets

Tablets containing 50 mg of 6-nicotinoylbenzoxazolinone

Preparation formula for 1000 tablets.

| | | |
|---|---|---|
| 6-Nicotinoylbenzoxazolinone | 50 g | |
| Wheat starch | 15 g | |
| Cornstarch | 15 g | |
| Lactose | 65 g | |
| Magnesium stearate | 2 g | |
| Silica | 1 g | |
| Hydroxypropyl cellulose | 2 g | |

We claim:

1. The compound selected from those having the formula (I):

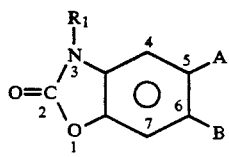

(I)

in which:

R$_1$ represents a hydrogen atom or a lower alkyl group, and (1) A represents a hydrogen atom, and in this case B represents a group CO—G, G being selected from:
a heteroaryl group selected from furan, indole, pyrrole, pyridine, quinoline, isoquinoline and benzofuran, optionally substituted with one or more lower alkyl or lower alkoxy groups or a halogen atom,
a linear or branched lower alkyl group substituted with a carboxyl group,
a linear or branched lower alkenyl group substituted with a carboxyl group, and
a phenyl or naphthyl group substituted with a carboxyl group,
or (2) A forms with B a group CO(CH$_2$)$_n$CH(CH$_3$) with n being an integer equal to 1, 2, 3 or 4, the CO group being attached to the aromatic ring of the benzoxazolinone at the 5- or 6-position,
as well as, where appropriate, its isomers and, when the compound of formula (I) possesses a carboxylic acid group, its addition salts within a pharmaceutically acceptable base, and, when the compound of formula (I) contains a basic group, its addition salts with a pharmaceutically acceptable acid, it being understood that lower alkyl, lower alkoxy and lower alkenyl mean linear or branched groups comprising 1 to 6 carbon atoms inclusive.

2. A compound as claimed in claim 1 in which B represents a group CO—G with G being heteroaryl selected from furan, indole, pyrrole, pyridine, quinoline, isoquinoline and benzofuran, optionally substituted with one or more lower alkyl or alkoxy groups or a halogen atom, as well as, when G comprises a basic group, its addition salts with a pharmaceutically acceptable acid.

3. A compound as claimed in claim 1 in which B represents a group CO—G with G being linear or branched lower alkyl substituted with a carboxyl group, and where appropriate its isomers, as well as its addition salts with a pharmaceutically acceptable base.

4. A compound as claimed in claim 1 in which B represents a group CO—G with G being linear or branched lower alkenyl substituted with a carboxyl group, and its isomers, as well as its addition salts with a pharmaceutically acceptable base.

5. A compound as claimed in claim 1 in which B represents a phenyl or naphthyl group substituted with a carboxyl group, as well as its addition salts with a pharmaceutically acceptable base.

6. A compound as claimed in claim 1 in which A forms with B a group CO(CH$_2$)$_n$CH(CH$_3$) with n being an integer equal to 1, 2, 3 or 4, the CO group being attached to the aromatic ring of the benzoxazolinone at the 5- or 6-position, as well as its isomers.

7. A compound as claimed in claim 2 in which B represents a group CO—G with G being a heterocycle selected from furan and pyridine, as well as, when G represents pyridine, its addition salts with a pharmaceutically acceptable acid.

8. A pharmaceutical composition useful in treating ischemic or stroke containing as active principle an effective amount of a compound as claimed in claim 1, in combination with pharmaceutically-acceptable, excipient or vehicle.

9. A method of treating a living animal afflicted with arterial ischemic attack or stroke comprising the step of administering to the said living animal an amount of a compound of claim 1, which is effective for the alleviation of said condition.

* * * * *

UNITED STATES PATENT AND TRADEMARK OFFICE
CERTIFICATE OF CORRECTION

PATENT NO. : 5,147,883

DATED : Sep. 15, 1992

INVENTOR(S) : Hocine Aichaoui, Daniel Lesieur, Charles Lespagnol, Michelle Devissaguet, Beatrice Guardiola It is certified that error appears in the above-identified patent and that said Letters Patent is hereby corrected as shown below:

Title Page, [75] Inventors: "Aichaioui," should read -- Aichaoui,--

Column 5, approximately line 43; "$^{-1}:\mu$ NH;" should read -- $^{-1}:\nu$ NH; --.

Column 5, approximately line 47; "aromatic" should read --magnetic--.

Column 6, line 1; "hydrochloride" should read --hydrochloric--.

Column 6, approximately line 61; "$^{-1}:\mu$ OH:" should read -- $^{-1}:\nu$ OH --.

Column 7, approximately line 18; "$^{-1}:\mu$ NH" should read -- $^{-1}:\nu$ NH --.

Column 7, approximately line 28; "-methybenzoxazolinon-" should read -- methylbenzoxazolinon- --.

Column 7, line 42; "$^{-1}:\mu$ OH" should read -- $^{-1}:\nu$ OH --.

Column 7, approximately line 47; "doublet," should read -- singlet, --.

Column 7, line 65; "$^{-1}:\mu$ OH" should read -- $^{-1}:\nu$ OH --.

Column 8, line 27; "(ketonic" should read -- (ketonic) --.

Column 8, approximately lines 48-53; after the colon ":" change "$\lambda$" to --$\nu$-- in each instance (6).

Column 8, line 52; "(ketonic" should read -- (ketonic)--.

Column 9, lines 8-11, in each instance, a total of 4, change "$^{-1}:\lambda$" to -- $^{-1}:\nu$ --.

Column 9, lines 33-37, in each instance, a total of(5), change "$^{-1}:\lambda$" to --$^{-1}:\nu$ --.

Column 9, lines 64/65, in each instance, a total of (2), change "$^{-1}:\lambda$" to -- $^{-1}:\nu$--.

Column 10, approximately lines 24/25; in each instance, a total of (2), change "$^{-1}:\lambda$" to -- $^{-1}:\nu$ --.

UNITED STATES PATENT AND TRADEMARK OFFICE
CERTIFICATE OF CORRECTION

PATENT NO. : 5,147,883

DATED : Sep. 15, 1992

INVENTOR(S) : Hocine Aichaoui, Daniel Lesieur, Charles Lespagnol, Michelle Devissaguet, Beatrice Guardiola It is certified that error appears in the above-identified patent and that said Letters Patent is hereby corrected as shown below:

Column 10, lines 45/46; in each instance, a total of (2), change "$^{-1}:\lambda$" to -- $^{-1}:\nu$ --.

Column 11, lines 24-26; in each instance, a total of (3), change "$^{-1}:\lambda$" to -- $^{-1}:\nu$ --.

Column 11, lines 44-46; in each instance, a total of (3), change "$^{-1}:\lambda$" to -- $^{-1}:\nu$ --.

Column 11, lines 64/65; in each instance, a total of (2), change "$^{-1}:\lambda$" to -- $^{-1}:\nu$ --.

Column 12, line 18; "Quinolycarbonyl" should read --Quinolylcarbonyl--.

Column 12, line 22; "quionolinecarbonyl" should read -- quinolinecarbonyl --.

Column 12, line 46; "isoquinoinecaarbonyl" should read -- isoquinolinecarbonyl --.

Column 12, approximately line 65; "indolylcarbonyl" should read -- indolyl) --.

Column 14, line 20; "within" should read -- with --.

Column 14, line 59; "ischemic" should read -- ischemia --.

Signed and Sealed this

Nineteenth Day of October, 1993

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,147,883

Page 1 of 2

DATED : Sep. 15, 1992

INVENTOR(S) : Hocine Aichaoui, Daniel Lesieur, Charles Lespagnol, Michelle Devissaguet, Beatrice Guardiola It is certified that error appears in the above-identified patent and that said Letters Patent is hereby corrected as shown below:

Title Page, [75] Inventors: "Aichaioui," should read -- Aichaoui,--

Column 5, approximately line 43; "$^{-1}$:μ NH;" should read -- $^{-1}$:ν NH; --.

Column 5, approximately line 47; "aromatic" should read --magnetic--.

Column 6, line 1; "hydrochloride" should read --hydrochloric--.

Column 6, approximately line 61; "$^{-1}$:μ OH:" should read -- $^{-1}$:ν OH --.

Column 7, approximately line 18; "$^{-1}$:μ NH" should read -- $^{-1}$:ν NH --.

Column 7, approximately line 28; "-methybenzoxazolinon-" should read -- methylbenzoxazolinon- --.

Column 7, line 42; "$^{-1}$:μ OH" should read -- $^{-1}$:ν OH --.

Column 7, approximately line 47; "doublet," should read -- singlet, --.

Column 7, line 65; "$^{-1}$:μ OH" should read -- $^{-1}$:ν OH --.

Column 8, line 27; "(ketonic" should read -- (ketonic) --.

Column 8, approximately lines 48-53; after the colon ":" change " λ " to -- ν -- in each instance (6).

Column 8, line 52; "(ketonic" should read -- (ketonic)--.

Column 9, lines 8-11, in each instance, a total of 4, change "$^{-1}$:λ " to -- $^{-1}$:ν --.

Column 9, lines 33-37, in each instance, a total of (5), change "$^{-1}$:λ " to -- $^{-1}$:ν --.

Column 9, lines 64/65, in each instance, a total of (2), change "$^{-1}$:λ " to -- $^{-1}$:ν --.

Column 10, approximately lines 24/25; in each instance, a total of (2), change "$^{-1}$:λ " to -- $^{-1}$:ν --.

UNITED STATES PATENT AND TRADEMARK OFFICE
CERTIFICATE OF CORRECTION

PATENT NO. : 5,147,883

DATED : Sep. 15, 1992

INVENTOR(S) : Hocine Aichaoui, Daniel Lesieur, Charles Lespagnol, Michelle Devissaguet, Beatrice Guardiola It is certified that error appears in the above-identified patent and that said Letters Patent is hereby corrected as shown below:

Column 10, lines 45/46; in each instance, a total of (2), change "$^{-1}:\lambda$" to -- $^{-1}:\nu$ --.

Column 11, lines 24-26; in each instance, a total of (3), change "$^{-1}:\lambda$" to -- $^{-1}:\nu$ --.

Column 11, lines 44-46; in each instance, a total of (3), change "$^{-1}:\lambda$" to -- $^{-1}:\nu$ --.

Column 11, lines 64/65; in each instance, a total of (2), change "$^{-1}:\lambda$" to -- $^{-1}:\nu$ --.

Column 12, line 18; "Quinolycarbonyl" should read --Quinolylcarbonyl--.

Column 12, line 22; "quionolinecarbonyl" should read -- quinolinecarbonyl --.

Column 12, line 46; "isoquinoinecaarbonyl" should read -- isoquinolinecarbonyl --.

Column 12, approximately line 65; "indolylcarbonyl" should read -- indolyl)carbonyl --.

Column 14, line 20; "within" should read -- with --.

Column 14, line 59; "ischemic" should read -- ischemia --.

This certificate supersedes Certificate of Correction issued October 19, 1993.

Signed and Sealed this

Seventeenth Day of October, 1995

Attest:

BRUCE LEHMAN

Attesting Officer

Commissioner of Patents and Trademarks